(12) United States Patent
Williams et al.

(10) Patent No.: US 6,394,999 B1
(45) Date of Patent: May 28, 2002

(54) LASER EYE SURGERY SYSTEM USING WAVEFRONT SENSOR ANALYSIS TO CONTROL DIGITAL MICROMIRROR DEVICE (DMD) MIRROR PATTERNS

(75) Inventors: Roy E. Williams, Collierville; James F. Freeman; Jerre M. Freeman, both of Memphis, all of TN (US)

(73) Assignee: Memphis Eye & Cataract Associates Ambulatory Surgery Center, Memphis, TN (US)

(*) Notice: Subject to any disclaimer, the term of this patent is extended or adjusted under 35 U.S.C. 154(b) by 0 days.

(21) Appl. No.: 09/524,312

(22) Filed: Mar. 13, 2000

(51) Int. Cl.⁷ ................................. A61B 18/18
(52) U.S. Cl. ............... 606/5; 606/4; 356/2; 351/212; 128/898
(58) Field of Search .............. 606/4–6, 10–13; 356/2, 4.09, 24, 27; 128/898; 351/212

(56) References Cited

U.S. PATENT DOCUMENTS

| | | | |
|---|---|---|---|
| 4,682,025 A | 7/1987 | Livingston et al. | 250/201 |
| 5,098,426 A * | 3/1992 | Sklar et al. | 606/5 |
| 5,229,889 A | 7/1993 | Kittell | 359/849 |
| 5,233,174 A | 8/1993 | Zmek | 250/201.9 |
| 5,410,397 A | 4/1995 | Toeppen | 356/121 |
| 5,624,437 A * | 4/1997 | Freeman et al. | 606/12 |
| 5,677,783 A | 10/1997 | Bloom et al. | 359/224 |
| 5,752,950 A * | 5/1998 | Frey et al. | 606/12 |
| 5,777,719 A * | 7/1998 | Williams et al. | 351/212 |
| 5,782,822 A * | 7/1998 | Telfair et al. | 606/5 |
| 5,825,476 A | 10/1998 | Abitol et al. | 356/124 |
| 5,879,346 A | 3/1999 | Waldman et al. | 606/9 |
| 5,912,731 A | 6/1999 | DeLong et al. | 356/121 |
| 6,099,522 A * | 8/2000 | Knopp et al. | 606/10 |
| 6,129,722 A * | 10/2000 | Ruiz | 606/5 |
| 6,299,309 B1 * | 10/2001 | Ruiz | 351/212 |

OTHER PUBLICATIONS

Paper entitled "Photorefractive keratectomy; a technique for laser refractive surgery" by C.R. Munnerlyn, S. J. Koons, and J. Marshall, in J. Cataract Refract. Surg.14, pp. 46–52 (1988).

Paper entitled "Anatomically accurate, finite model eye for optical modeling" by H. Liou and N.A. Brennan, in J. Opt. Soc. Am. A, vol. 14, No. 8, (1997), pp. 1684–1695.

(List continued on next page.)

*Primary Examiner*—Linda C. M. Dvorak
*Assistant Examiner*—A. Farah
(74) *Attorney, Agent, or Firm*—David P. Gordon; David S. Jacobson; Thomas A Gallagher

(57) ABSTRACT

A system and method for performing corneal ablation or reshaping with a laser in order to correct aberrations in the optical system of the eye utilizes a wavefront sensor which defines a wavefront correction for the eye and then, based upon that defined wavefront correction, drives a digital micromirror device (DMD) which modulates a laser beam to the eye to perform the correction. As the DMD is a 2-D array of individually controlled mirrors, and the wavefront sensor analysis can provide a sequence of two dimensional arrays of values which together define the wavefront correction for the eye, the combination of the two produces a method for correcting the corneal surface. The system may be operated in either of two manners to achieve optimum refractive corrections: (1) off-line measurement of the eye optical system via the wavefront sensor followed by DMD-based laser refractive surgery, or (2) real-time measurement of the eye optical system via the wavefront sensor which directs a DMD-based laser refractive surgery system.

27 Claims, 7 Drawing Sheets

(2 of 7 Drawing Sheet(s) Filed in Color)-

OTHER PUBLICATIONS

Paper entitled "Custom photorefractive keratectomy ablations for the correction of spherical and cylindrical refractive error and higher–order aberration" by J. and R.W. Snyder in J. Opt. Sci. Am. A, vol. 15, No. 9, (1998), pp. 2572–2579.

Paper entitled "Control of Micromachined Deformable Mirrors" by Agronin, Hadaegh, Kaiser (of Jet Propulsion Labs at Cal. Inst. of Tech.) and Wang (Dept of Elect. Eng, Univ of Cal), May 1992, 22 pages.

Paper entitled "Customized ablations; the future is close", by Irving J. Arons, Feb. 15, 2000 in Ocular Surgery News, a SLACK Incorporated Newspaper, 7 pages.

Copy of Internet webpage, for Laser Techniques at www.excimer.de/lasertechnik/e_holmium_body.html, 1 page, downloaded Jan. 21, 2000.

Paper entitled "Effects of Pupillary dilation on Corneal Optical Aberrations after Photorefractive Keratectomy" by Carlos E. Martinez, Raymond A. Applegate, Stephen D. Kylce, Marguerite B. McDonald, Jan P. Medina and Howard C. Howland, in ARCH Opthalmol/vol. 116, Aug. 1998, pp. 1053–1062.

Abstract of "Changes in Corneal Aberration Structure after photorefractive keratectomy" by Martinez, Applegate, Howland, Klyce, McDonald and Medina, at at ISU Eye Center, New Orleans.LA.

Paper entitled "Objective measurement of wave aberrations of the human eye with the use of a Hartmann–Shack wave–front sensor" by Liang, Grimm, Goetz, and Bille, in J. Opt. Soc. Am. A, vol. 11, No. 7, Jul. 1994, pp. 1949–1957.

Copy of article on Internet Website page entitled "Wavefront measurements may replace eye charts" by Deena Beasley, Feb. 13, 2000, 3 pages.

Product Information Brochure from LADARVISION for "True Custom Cornea, the magic of wavefront sensing, only from Autonomous.", from Autonomous Technologies Corporation, 1999, 7 pages.

Product Information and Specifications for Wavescope, a Wavefront sensor system, WFS–01 table top optical wavefront sensor, from Adaptive Optics Associates, Inc. (AOA), 1 page. 1997.

Copy of Internet webpage, www.tiac.net/users/XINETICS, for Xinetics deformable mirrors, 1 page, downloaded Jan. 21, 2000.

Copy of Internet webpage, op.ph.ic.uk/bimorph/application for "Adaptive Laser Scanner", 1 page, downloaded Jan. 21, 2000.

* cited by examiner

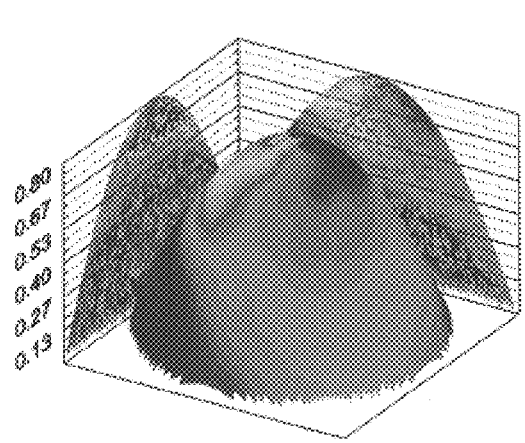
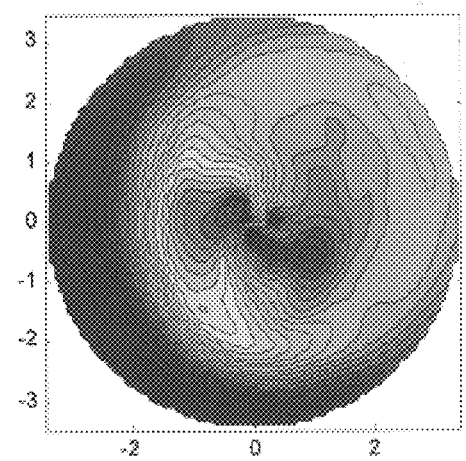
Fig. 3                                    Fig. 4
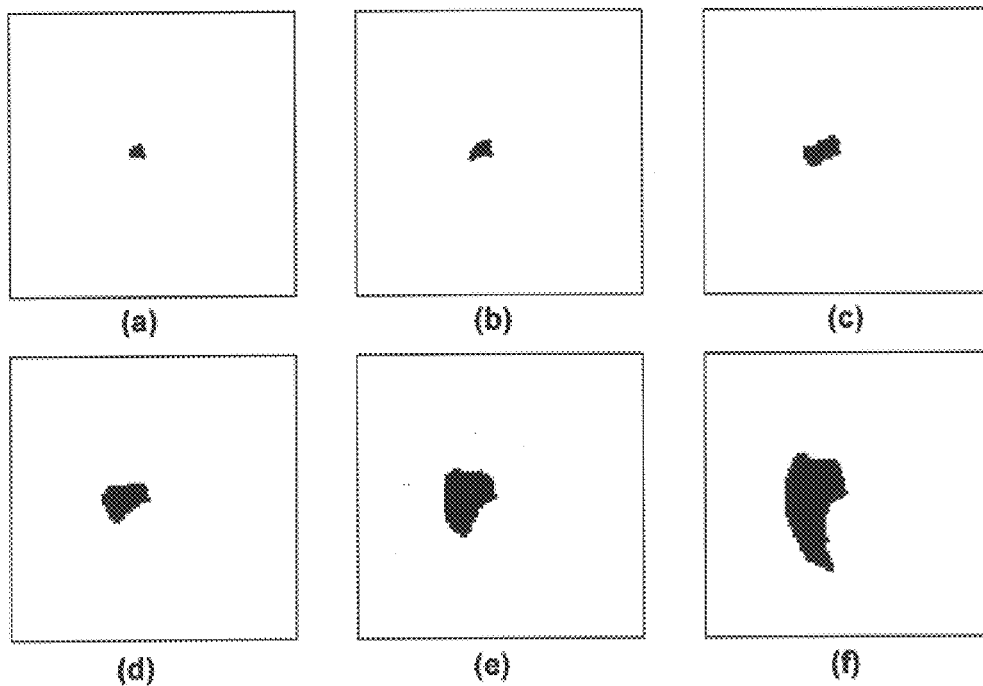
Fig. 6

LASER EYE SURGERY SYSTEM USING WAVEFRONT SENSOR ANALYSIS TO CONTROL DIGITAL MICROMIRROR DEVICE (DMD) MIRROR PATTERNS

The U.S. Government has a paid-up non-exclusive license in this invention as provided for by Grant No. R44 EY11587 awarded by the National Eye Institute of the National Institute of Health.

BACKGROUND OF THE INVENTION

1. Field of the Invention

This invention relates broadly to eye surgery. More particularly, this invention relates to refractive laser systems for eye surgery.

2. State of the Art

The laser refractive surgery (or laser keratectomy) field has exploded over the past few years with many new lasers and algorithms to correct human vision. Systems are now using laser wavelengths from the ultraviolet (excimer) to the infrared to change the shape of the cornea in a calculated pattern which makes it possible for the eye to focus properly. For example, in the treatment of myopia, the excimer laser is used to remove or ablate tissue from the cornea in order to flatten its shape. Infrared (IR) energy is also used by some companies to treat myopia by reshaping the corneal tissue by a "thermal" method as opposed to ablation with the excimer wavelength. The correction of hyperopia is produced by steepening the cornea by removing tissue at the outer edges of the cornea (excimer) or by reshaping the cornea at the outer edges (IR energy). The correction of astigmatism, both myopic and hyperopic, requires the laser to remove (as done by the excimer laser) or reshape (as done by the IR laser) tissue in a more complex pattern. Laser corneal reshaping procedures are effective for correcting impaired visual acuity, but many researchers now believe this effectiveness needs to be improved. The proper model and delivery of the laser energy for removing or altering the tissue has been a major discussion recently as postoperative studies are indicating that current procedures may actually be inducing aberrations in the eye optical system.

Initial systems approved by the FDA implement the refractive corrections by a broadbeam approach; i.e., by delivering beam-shaped laser energy based on thin lens theory and paraxial optics applied to a single spherical surface. The beam is shaped by a motorized iris (myopia and hyperopia) and motorized slit (astigmatism) based on profiles derived through Munnerlyn's derivation (C. R. Munnerlyn, S. J. Koons, and J. Marshall, "Photorefractive keratectomy: a technique for laser refractive surgery", *J. Cataract Refract. Surg.* 14, 46–52 (1988)). Systems using this approach are currently marketed by VISX and Summit. More than one million eyes have been treated in this manner in the United States. However, this approach is limited, as it symmetrically treats a broad area of the cornea all at one time. Eye topography maps and, more recently, wavefront analysis reveal that the cornea is a very complex structure with many minute variations across its surface. The broadbeam laser approach cannot correct these minute variations.

A more recent approach to laser keratectomy uses a scanning laser spot system in which a small laser spot (typically 0.5-mm to 1.0-mm in diameter) is scanned across the cornea in a predetermined pattern to achieve refractive corrections. These systems differ in that they are more flexible than the broadbeam approach. With the control of a small spot, different areas of the cornea can be shaped independently of other areas. The scanning spot approach, therefore, allows for the laser beam to be moved in a specific pattern over the cornea to more particularly correct the shape of the cornea. However, there are several problematic issues with scanning spot systems.

First is the issue of treatment time. Scanning spot systems require longer refractive surgery times. The scanning spot is a slower approach since the small laser spot has to be moved over a wide surface (up to 10-mm for hyperopia). The scanning spot system typically delivers several hundred spots per treatment layer, and consequently treatment times are generally long. The broadbeam approach is much quicker as the entire cornea is treated with each laser pulse, or treatment layer.

Second is the issue of safety. The broadbeam laser is inherently safe from a treatment interruption standpoint because the cornea is treated symmetrically for each pulse; the iris represents a circle and the slit represents a rectangle so that every point on the cornea being treated is treated the same with each laser pulse. If the procedure is interrupted, there will always be some symmetrical spherical correction which can be continued more easily at a later time. However, the scanning spot, with its small spot size, cannot cover the entire corneal surface with one laser pulse. Thus, if an interruption occurs, there is no guarantee of a complete corneal etch for a layer at the point of interruption. Continuation at the point of interruption would be difficult.

Third is the issue of tracking. In the scanning spot system the eye needs to be tracked very carefully in order to deliver the spot to the correct point on the cornea as the eye moves. This is not as much of a problem in the broadbeam system as a broader area is treated with each pulse.

Fourth is the issue of surface roughness. The necessary overlap of laser spots tends to create roughness in the resulting etch. While it is necessary to overlap spots to provide complete coverage for a given ablation zone, regions of overlap will be ablated at twice the etch depth per pulse. The smoothness of the ablated volume is dependent on the spot overlap and to a lesser extent, the ratio of spot diameter and ablation zone diameter. This problem is not seen in the broadbeam approach.

Current FDA-approved refractive laser systems do not directly use eye-modeling systems, such as corneal topographers or wavefront sensors, to create an individual treatment profile for a patient's eye. Rather, a topographic map is used indirectly by the surgeon in optimizing the treatment plan (diopter correction and astigmatic axis). More recently, eye contour topography has been used to more accurately provide refractive correction. There are systems currently going through FDA trials that do use corneal topographic surface data to directly guide the laser treatment algorithm. This is accomplished using a scanning laser spot, as current broadbeam laser refractive surgery systems cannot provide the laser beam detail required to use the topographic map data. Using the scanning spot system, each eye is individually analyzed as to its contour before ablation is applied. The goal with these systems is to take into account the varying degrees of curvature and height variations across the corneal surface, as opposed to assuming a perfect spherical surface as is currently done in broadbeam systems. Once these curvatures and height variations are determined by eye topography, they can be integrated with the refraction correction derivation of Munnerlyn to create customized ablation patterns for each individual eye.

The corneal topography approach has a drawback in that only measurements of the cornea are used. However, the eye is a complex optical system of which the cornea is only one component. Thus, even corneal topography information when combined with the current FDA-approved refraction equation, is not capable of suggesting what correction must be made to the corneal shape in order to optimally correct the overall aberration of the eye's optical system.

There have been several recent approaches to the above problems. First, by expanding the mathematical equations for refraction correction to include higher order effects, coma (3rd order) and spherical (4th order) aberrations can be reduced. See C. E. Martinez, R. A. Applegate, H. C. Howland, S. D. Klyce, M. B. McDonald, and J. P. Medina, "Changes in corneal aberration structure after photorefractive keratectomy," *Invest. Ophthalmol. Visual Sci. Suppl.* 37, 933 (1996). Second, by improving schematic model eyes to include higher order aberrations, these new models can provide insight into how the various elements of the eye optical system correlate to affect visual performance. For example, there is a general consensus that the negative asphericity of the normal cornea contributes a negative aberration content. The negative aberration is compensated by a positive aberration contribution from the gradient index nature of the lens. See H. Liou and N. A. Brennan, "Anatomically accurate, finite model eye for optical modeling," *J. Opt. Soc. Am. A,* Vol. 14, 1684–1695 (1997). The convergence of work on modeling the human optical system with more accurate mathematical descriptions for refraction correction has led to the development of advanced ablation profile algorithms that treat the cornea as the first aspheric element in an optical system. See J. Schwiegerling and R. W. Snyder, "Custom photorefractive keratectomy ablations for the correction of spherical and cylindrical refractive error and higher-order aberration," *J. Opt. Soc. Am. A,* Vol. 15, No. 9, 2572–2579 (1998).

In view of the recent work on viewing the cornea as an element of a larger optical system, and basing corneal correction with respect to this relation, it is desirable to provide a system and method for laser ablation or reshaping which will provide superior optical results.

SUMMARY OF THE INVENTION

It is therefore an object of the invention to provide a system and method for laser ablation or reshaping of the eye which considers higher order aberrations of the eye.

It is another object of the invention to provide a laser ablation or reshaping system and method which treats a broad area of the cornea at one time.

It is a further object of the invention to provide a laser ablation or reshaping system and method more flexible than the broadbeam approach of the prior art.

It is an additional object of the invention to provide a system and method which is capable of directing the laser beam in an asymmetric pattern over the cornea to more particularly correct corneal shape.

It is also an object of the invention to provide a laser ablation or reshaping system and method which can be operated and performed relatively quickly.

It is still another object of the invention to provide a laser ablation or reshaping system and method which is inherently safe from a treatment interruption standpoint.

It is still a further object of the invention to provide a laser ablation or reshaping system and method which does not require advanced high speed tracking of the eye as required in the scanning spot approach.

It is yet another object of the system to provide a laser ablation or reshaping system and method which will significantly reduce the corneal surface roughness seen in other approaches.

In accord with these objects, which will be discussed in detail below, a system and method for performing corneal ablation or reshaping with a laser in order to correct aberrations in the optical system of the eye utilizes a wavefront sensor which defines a wavefront correction for the eye and then, based upon that defined wavefront correction, drives a digital micromirror device (DMD) which modulates a laser beam to the eye to perform the correction. As the DMD is a two dimensional (2-D) array of individually controlled mirrors, and the wavefront sensor analysis can provide a sequence of 2-D arrays of values, the combination of the two produces a method for correcting the corneal surface. The system may be operated in either of two manners to achieve optimum refractive corrections: (1) off-line measurement of the eye optical system via the wavefront sensor followed by DMD-based laser refractive surgery, or (2) real-time measurement of the eye optical system via the wavefront sensor which directs a DMD-based laser refractive surgery system.

With this system and method, the eye surface may be corrected in a manner superior to prior art systems and methods. Wavefront sensing provides an overall refractive analysis of the entire eye optical system, e.g., taking into account the cornea, the lens, the vitreous and the retina. The result of a wavefront sensor analysis yields a waveform model which represents a nearly perfect refraction correction. This provides a superior analysis of the eye relative to the current topography systems which only analyze the cornea. In addition, the use of a DMD to then correct the eye in accord with the wavefront model provides a system which has none of the limitations associated with prior art broadbeam systems and scanning spot systems.

Additional objects and advantages of the invention will become apparent to those skilled in the art upon reference to the detailed description taken in conjunction with the provided figures.

BRIEF DESCRIPTION OF THE DRAWINGS

The file of this patent contains drawings executed in color. Copies of this patent with the color drawings will be provided by the Patent and Trademark Office upon request and payment of the necessary fee.

FIG. 3 is a color representation of a three-dimensional image of a wavefront analysis;

FIG. 4 is a two dimensional color topographic image providing the same information provided in FIG. 3;

FIGS. 6a–6f are dichromatic ablation or reshaping patterns associated with the topographic image of FIG. 4;

DETAILED DESCRIPTION OF THE PREFERRED EMBODIMENTS

According to the invention, systems are provided for performing corneal ablation or reshaping with a laser in order to correct aberrations in the optical system of the eye. As described in more detail below, the systems utilize a wavefront sensor which creates a data file convertible into a sequence of two-dimensional (2-D) arrays of values that together define a wavefront correction for the optical system of the eye. Based upon the defined wavefront correction, a 2-D digital micromirror device (DMD) modulates a laser beam into corrective patterns for the cornea of the eye. The use of a DMD for modulating a laser beam during eye surgery is disclosed in U.S. Pat. No. 5,624,437 to Freeman et al., which is hereby incorporated by reference herein in its entirety. The system may be operated in either of two manners to achieve optimum refractive correction: (1) an off-line measurement of the eye optical system via the wavefront sensor, followed by DMD-based laser refractive surgery, or (2) real-time measurement of the eye optical system via the wavefront sensor which is coupled to a DMD-based laser refractive surgery system such that the wavefront sensor information controls, in real-time, the DMD to modulate the laser.

Figure 1:
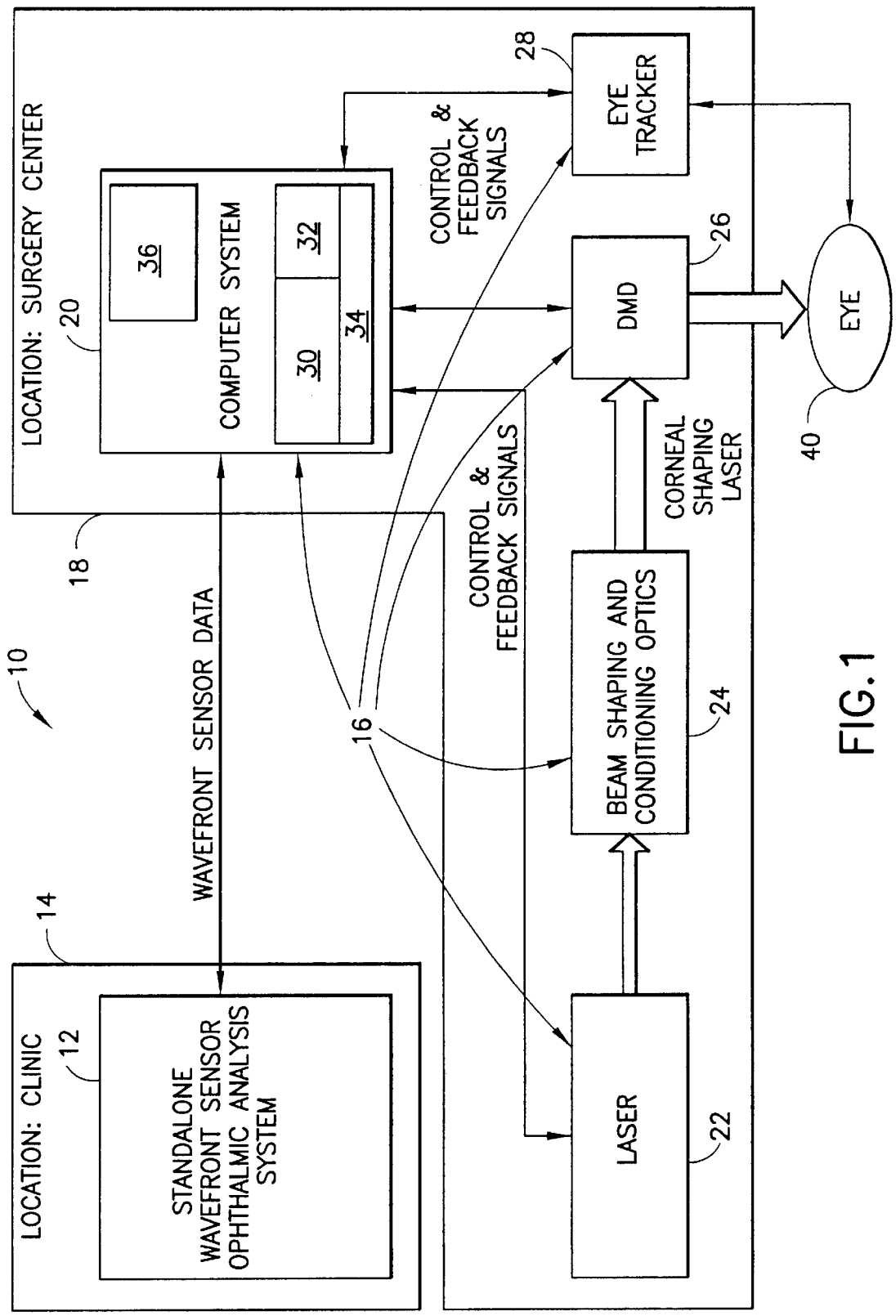
FIG. 1 is a block diagram of an off-line configuration of the laser ablation or reshaping system of the invention.

Referring now to FIG. 1, the off-line system 10 includes a preferably stand-alone wavefront sensor ophthalmic analysis system (or wavefront sensor system) 12 in a clinic 14, and an ophthalmic laser ablation or reshaping surgical system (laser system or surgery system) 16 in a surgical center 18. The laser system 16 generally includes a computer system 20, a laser 22, beam-shaping and conditioning optics 24, a digital micromirror device 26, and an eye tracker system 28. The two systems 12 and 16 may be in the same room, in different rooms in the same building, or in completely different locations from each other.

More particularly, the wavefront sensor system 12 measures the optical system of the eye 40 and provides data corresponding to a three dimensional image of the optical system of the eye, as shown in FIG. 3. The three-dimensional results are translated into an array of optical wavefront information that characterizes the entire optical system of the eye. This information is preferably either in the form of topographical data (i.e., the height values that need to be corrected to arrive at an optimized corneal shape), as shown in FIG. 4, or in optical power data (often referred to as K-readings). One such wavefront sensor system is disclosed in U.S. Pat. No. 5,777,719 to Williams, which utilizes a Hartmann-Shack sensor and which is hereby incorporated by reference herein in its entirety, and others are available or forthcoming from 20/10 Perfect Vision of Heidelberg, Germany; Technomed GmbH of Baesweiler, Germany; Bausch & Lomb Surgical of Claremont, Calif.; and Tracey Technologies.

Figure 2:
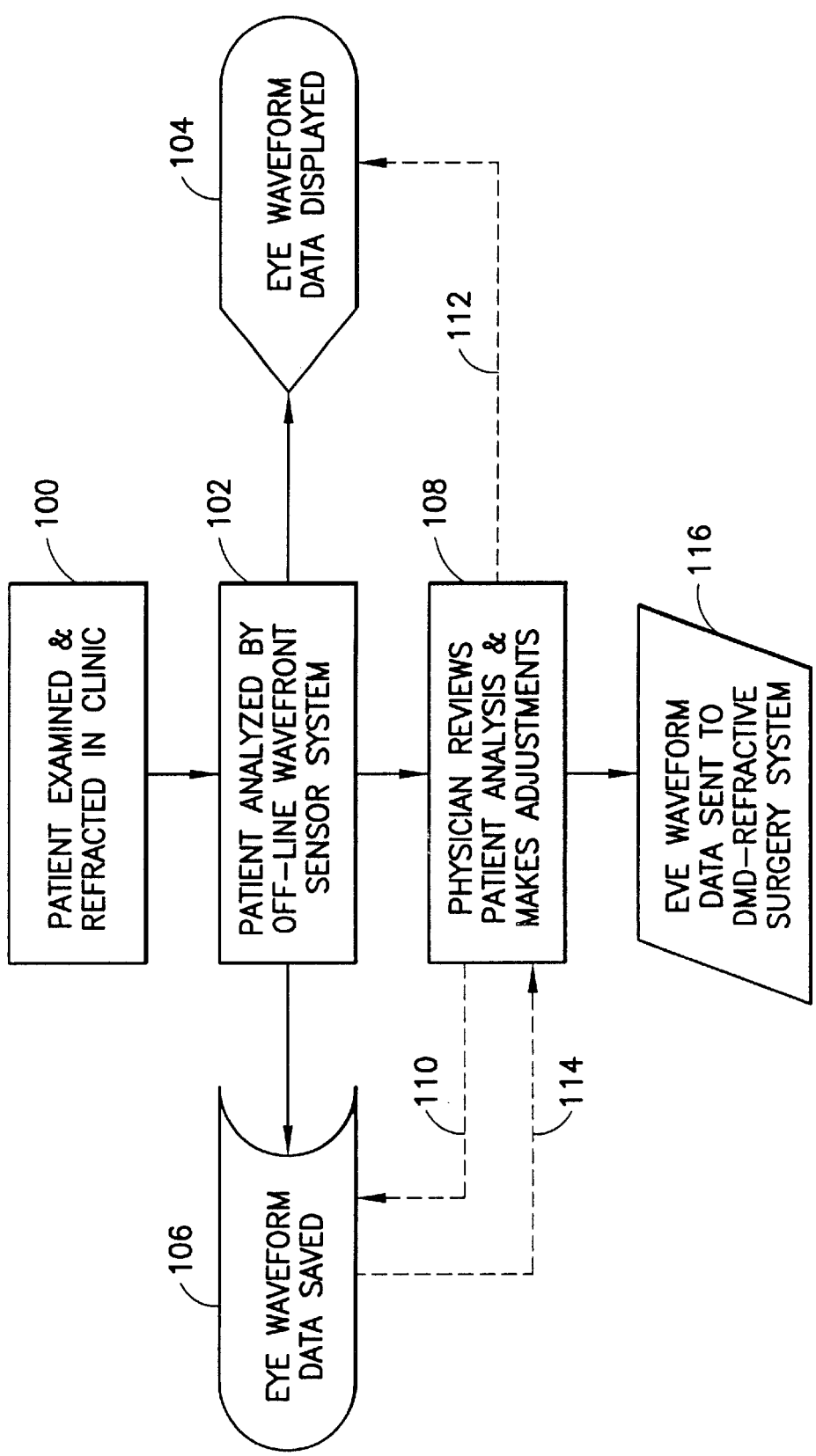
FIG. 2 is a flowchart of a wavefront sensor system for a non-surgical clinic in the off-line configuration of the laser ablation or reshaping system of the invention.

Turning to FIG. 2, in accord with the method of the invention and in accord with the off-line aspect of the first embodiment, a patient in a clinic environment is examined and refracted using known techniques. The patient is then analyzed by the wavefront sensor system at 102. The wavefront sensor system analysis generates a wavefront analysis data file incorporating a physiological alignment marker located on the corneal surface, preferably outside the area at which corneal ablation or reshaping takes place with a corrective laser, to allow for proper alignment later under the corrective laser. By way of example, the alignment marker may be a dye marker placed on the periphery of the cornea, e.g. at 3 o'clock, or a physiological structure such as the limbus. The wavefront analysis data file is optionally displayed at 104 on a video monitor, and also saved at 106 in electronic form (e.g., on removable media or in a network storage). A physician may review the wavefront analysis at 108, and is able, though not required, to make adjustments to the data file at 110 (and consequently to the data displayed at 112). The physician also has the option to recall at 114 from saved data the pre-adjusted data file, i.e., to discard all adjustments made such that the data file may be re-adjusted or such that it remains in original form. Once the physician is satisfied with the data file, the final data file is transferred at 116 to the surgery system 16.

Referring back to FIG. 1, the surgery system 16 is preferably substantially similar to the laser beam modulating apparatus disclosed in U.S. Pat. No. 5,624,437, previously incorporated by reference herein. As previously mentioned, the surgery system 16 generally includes a computer system 20, a laser 22 for producing a laser beam capable of making refractive corrections, an optical system 24 for shaping and conditioning the laser beam, a DMD 26, and an eye tracking system 28.

More particularly, the computer system 20 includes a computer 30 including a microprocessor, a video controller board 32, a DMD controller 34 which is capable of manipulating the mirrors of the DMD into either an ON or OFF position, and a video monitor 36. The computer 30 is capable of receiving and processing the wavefront information, controlling the video controller board 32, monitoring and controlling external devices (safety switches, surgery footswitch, shutters, laser interface, etc.), and providing information to the user. A current preferred computer 30 is a Dell Workstation Model 6550, with Dual 550 MHZ Pentium III Xeon Processors, 128 Mbytes of RAM, and 9.1 GByte SCSI hard drive, though other computers can likewise be used. The video controller board 32, e.g., the LCD555PCI video card available from Inside Technology (P/N 710920), supplies video signals to the DMD controller 34 as well as to the video monitor 36. The DMD controller 34 includes a video receiver card, preferably a Texas Instruments, Inc. XGA video receiver card (P/N 4186152-0001), which receives video information from the video controller board 32 and a video driver card, preferably a Texas Instruments, Inc. XGA video driver card (P/N 4186137-0001), which converts the video information into signals that drive the appropriate mirrors in the DMD 26 to the ON or OFF state. The DMD controller 34 may be provided external of the computer 30 or may be provided as a card or set of cards within the computer.

Figure 5:
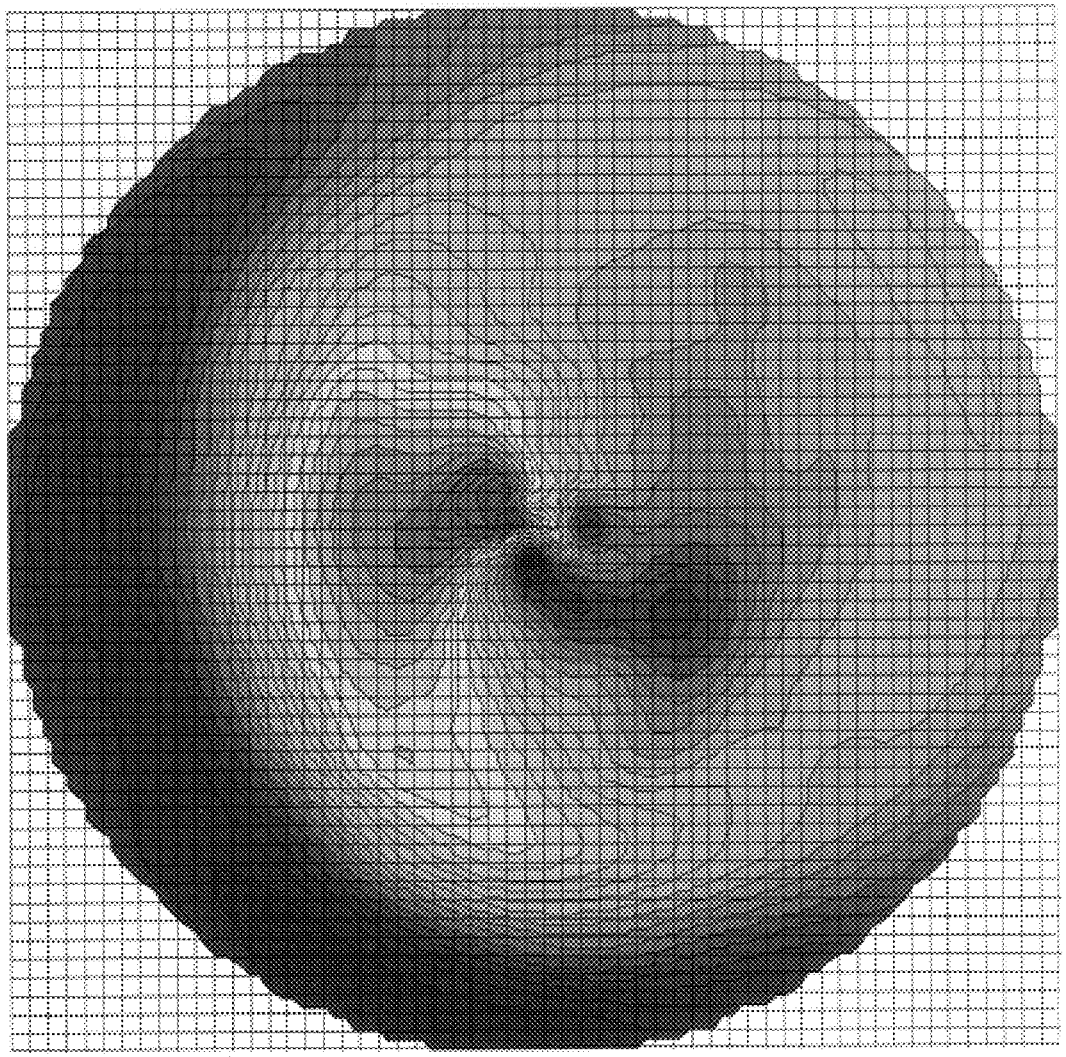
FIG. 5 is an illustration of a grid superimposed over the topographic image of FIG. 4, wherein each box of the grid represents 10 mirrors of the DMD in each of the X and Y directions; i.e., 100 mirrors per grid box.

System software is also provided which creates a plurality of dichromatic images from the wavefront image data file. Referring to FIG. 5, by superimposing a grid corresponding to the mirrors of the DMD (each box of the grid representing 10 mirrors in each of the X and Y directions) over the topographical image, a series of dichromatic images representing the topographical patterns in which the cornea is to be ablated can be created. FIGS. 6a–f illustrate six dichromatic images (out of many additional images) relating to the wavefront analysis data shown in FIGS. 4 and 5. The dichromatic images (or data representations thereof) are then provided in sequence to the video controller board 32 (one for each laser pulse) to cause display of the images on the video monitor 36 and also sent to the DMD controller 34 which causes the DMD mirrors to assume patterns in the shape of the dichromatic images. For example, in a black and white image, all black portions of the image may cause the associated DMD mirrors to assume an ON position (that is, to reflect laser energy to the cornea), while all white portions of the image may cause the associated mirrors to assume an OFF position (that is, to reflect laser energy away from the cornea and into a beam dump). Current software is developed under LabView™; however, any suitable language (e.g., C, C++, etc.) can be used for the software development.

The laser system 22 is preferably an excimer laser (operating at 193 nm wavelength), or other commonly known type of laser suitable for broadbeam refractive laser surgery, such as 3 to 3.1 μm wavelength infrared energy. As disclosed in previously incorporated U.S. Pat. No. 5,624, 437, the DMD 26 is mounted in the optical path of a laser beam created by the laser 22. The DMD 26 is available from Texas Instruments, Inc., and is provided with a UV-transmissive window. The optical system 24 is provided between the laser system 22 and the DMD 26 and is preferably comprised of common, off-the-shelf optical components used to shape the laser beam (this can include beam expansion, collimation and homogenization), direct the laser beam to the DMD 26 for pattern control, and direct the laser beam from the DMD to the corneal surface of the eye 40. Such optical systems are well-known to those skilled in the art.

The eye tracking system 28 provides input to the DMD controller 34 such that the DMD is capable of accurately directing the patterned laser beam to a moving eye. In one approach, disclosed in U.S. Ser. No. 09/371,195, filed Aug. 10, 1999, and hereby incorporated by reference herein in its entirety, the eye tracking system 28 uses a CCD camera connected to the surgical microscope, an illuminator to illuminate the eye, and an algorithm to find the center of the pupil and compare it against the starting point of the procedure. The eye tracking system 28 is able to continually feed the eye movement information to the DMD video controller board 32 in order to offset the refraction correction pattern created by the mirrors of the DMD 26 such that the pattern is directed to the correct position based on the eye's last position. Other approaches to tracking the eye may also be used. For example, and not by way of limitation, target markers placed on the cornea (reflective or absorptive to certain wavelengths) may be monitored, laser spots aimed at the cornea (typically infrared energy) and monitored by a camera or other electronic means (such as quad detectors) may be tracked, or the retina may be tracked. It is noted that the eye tracking system need not be as sophisticated as that providing feedback to a scanning spot system, as here a relatively larger pattern is provided on the eye and the laser firing rate is considerably less than the spot scanning system.

Figure 7:
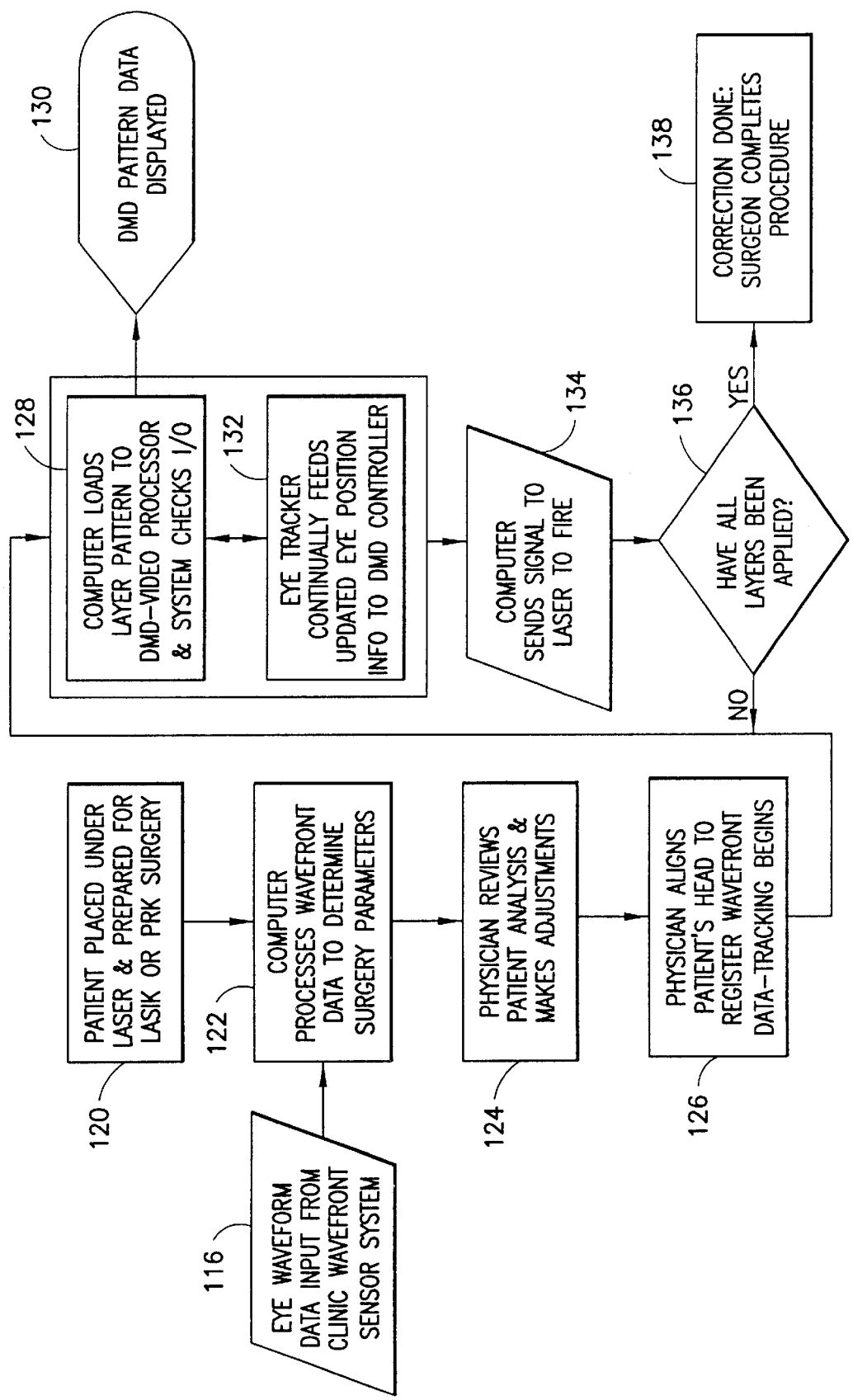
FIG. 7 is a flowchart of a laser ablation or reshaping procedure according to the off-line configuration of the laser ablation or reshaping system of the invention.

Turning now to FIG. 7, again in accord with a first embodiment of the method of the invention, the patient is placed under the refractive laser system and prepared for surgery using a photorefractive keratectomy (PRK) or laser keratomileusis in situ (LASIK) technique at 120. That is, in either technique the cornea stroma must be exposed prior to providing a laser beam to the cornea for corneal reshaping. In PRK, the epithelium of the cornea (approximately 40 to 55 microns) is removed by any effective means, e.g, with a laser, by scraping to expose the endothelium, or by chemical means such as with denatured alcohol. In LASIK, a flap is cut approximately 120 to 160 microns deep into the corneal stroma, and the flap is flipped back to expose the corneal stroma.

The computer 30 receives the wavefront data file provided at 116 (FIG. 2), and performs a refractive correction algorithm which is generally divided into five sections: (a) process the wavefront sensor data file at 122; (b) provide the processed wavefront information to the video controller board 32 and DMD controller 34, at 128, and update, at 132, the eye position information from the eye tracker 28; (c) check at 128 all input signals from external devices; (d) fire the laser at 134; and (e) loop back to (a) at 136 until the procedure is complete. Processes (a) through (c) can operate in parallel.

More particularly, part (a) of the above algorithm requires that the computer system receive and process at 122 the wavefront data file. As discussed above, the wavefront data file includes topographic information which is processed to create several layers of reshaping patterns. The computer system 20 receives the wavefront data file from the clinic at 116 and then processes at 122 the wavefront data file to calculate the number of layers/pulses and the pattern within each layer required to implement the correction; that is, the surgery parameters. The number of layers depends on the energy density used. For example, in excimer-based surgery, a 160 mJ/cm$^2$ is typically used which results in a nominal removal of 0.25 micron of tissue per pulse. Each pulse lasts approximately 10 nanoseconds in length. The number of pulses would differ for other energy densities and wavelengths, such as IR energy. The pattern of each layer is typically unique, and is sent to the mirrors of the DMD, thereby directing the laser beam to the appropriate position on the cornea.

A surgeon, at 124, preferably then reviews the wavefront analysis from the data file and the adjustments (if any) made thereto by the physician. The surgeon may also review each of the image patterns on the video monitor 36 and may make adjustments to the images (and thereby adjust the patterns of the laser beam) or approve the current associated patterns of laser ablation or reshaping.

Once the surgeon is satisfied with the patterns for laser ablation or reshaping of the corneal stroma, the surgeon aligns the patient's head, and thus the eye, at 126 to provide a starting point against which the actual position of the eye during surgery is registered, and the patterns are offset. This is accomplished by a heads-up-display (HUD) which provides a virtual image of a registration point directly on the cornea which is then aligned with the alignment marker used in the off-line wavefront measurement at 102. Multiple registration points and alignment markers may be aligned. Once this is complete, the eye tracking aspect of the computer takes over the alignment adjustment.

The computer 30 then has the video controller board 32 provide at 128 the appropriate pattern for correction of the first or topmost layer (generally at the location requiring the most ablation or reshaping throughout the entire cornea) of the exposed corneal stroma to the DMD controller 34 and, at 130, to the video monitor 36. The DMD controller 34 then adjusts the mirrors of the DMD 26 into the corresponding pattern such that a beam from the laser 22 will be directed to the cornea according to the pattern.

Then all input signals are checked at 128. Such input signals include, but are not limited to, laser status, safety switch status, gas cabinet sensor status (for gas-based lasers), safety shutter subsystem status, laser energy sensor status, nitrogen flow status, surgeon footswitch status, emergency stop switch status, surgeon joystick control status, exhaust plume tube position, and status indicator lights. More particularly, regarding laser status, the laser system sends a signal indicating that it is in a ready-to-fire condition. In addition, the laser cavity pressure, laser cavity temperature, and output laser energy from a previous laser pulse (where available) are also checked. Regarding safety switch status, a low voltage, low current signal (typically 5V) is sent to switches or sensors to confirm that the doors and panels on the laser system enclosure are in a closed position. Regarding gas cabinet sensor status, for gas-based lasers, a gas detection sensor is monitored to confirm that there is no gas (e.g., Argon Fluorine) leak. Regarding safety shutter subsystem status, there are at least two safety shutters that block the laser beam under certain conditions, and the computer monitors the shutters to confirm that they are in the appropriate position. Regarding laser energy sensor status, one or more sensors monitor the energy of the output of the laser and confirm that the energy is within an acceptable range. Regarding nitrogen flow status, nitrogen is often blown across the optical path to increase transmission efficiency from the laser to the eye. The flow is sensed and a signal is monitored indicated the state of flow. Regarding surgeon footswitch status, the surgeon controls the procedure with a footswitch. Typically, the footswitch must be in a depressed (or closed) position for the procedure to continue. Regarding emergency stop switch status, the switch is located near a microscope provided for monitoring the progress of the procedure and enables the surgeon or technician to press the switch and interrupt the procedure in the event of emergency. Regarding the surgeon joystick control status, the surgeon is provided with a joystick to move the patient and thereby the eye of the patient relative to and under the microscope. The signal of the joystick is monitored, and the laser may be configured to not fire while the joystick is providing a signal to move the patient relative to the microscope. Regarding the exhaust plume tube position, an exhaust tube is provided which removes the ablated tissue from above the eye after each laser pulse. The tube must be located just above the sterile surgical field to permit the laser to fire. Regarding the status indicator lights, the lights are monitored to confirm that all lights are in the appropriate condition for firing the laser. Other parameters may also be monitored and checked prior to firing the laser.

In addition, the eye tracking system 28 continually feeds eye location data to the DMD controller at 132, as described above. The last eye position location after the input parameters have been checked and approved is provided to the DMD controller 34. When required by movement of the eye relative to its starting point, the mirror pattern of the DMD is offset by the DMD controller 34 to direct the laser to the appropriate location on the eye.

The laser is then operated to fire a broadbeam pulse onto the mirrors of the DMD which then redirect laser energy only to those areas of the cornea identified for reshaping or ablating within that layer.

The process then repeats steps 128, 130, 132, and 134 for additional patterns for subsequent layers of ablation or reshaping. After the last (deepest) layer has been reshaped or ablated at 136 (e.g., such that all red, orange, and yellow layers in FIG. 4 have been ablated or reshaped to provide a higher order correction to the eye), the refractive corrective portion of the procedure is over and the surgeon completes the procedure, at 138. Completion requires either applying a contact lens over the exposed corneal stroma for PRK (until endothelium cell regrowth is complete) or repositioning the corneal flap for LASIK.

The above system and method provide a two-step approach for optimal refraction and laser correction of the eye.

Figure 8:
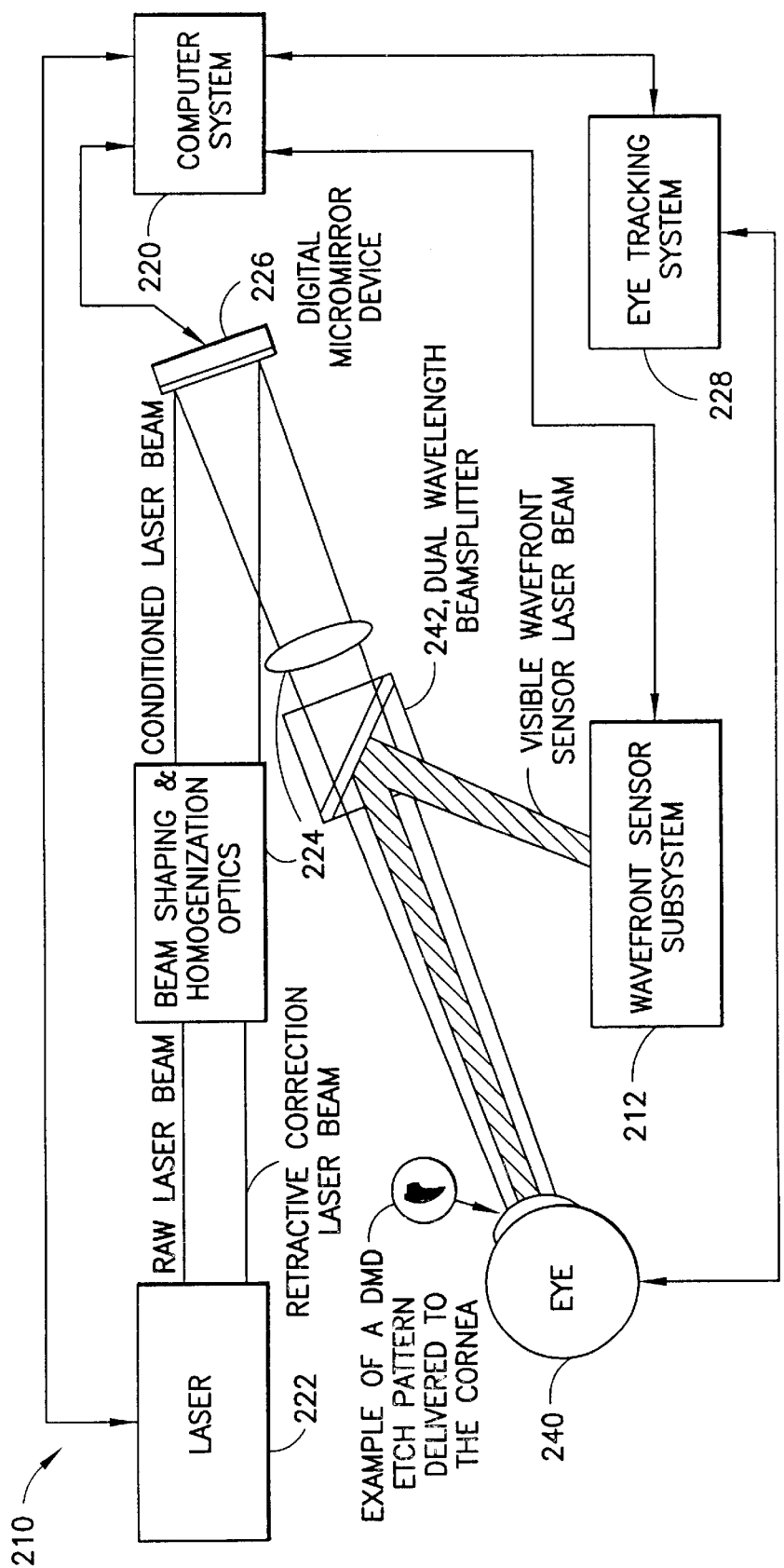
FIG. 8 is a block diagram of a real-time configuration of the laser ablation or reshaping system of the invention.

According to a second embodiment of the invention, the system may also be implemented in real-time; that is, as a one-step approach. Generally, the optical system of the eye is measured by a wavefront sensor system which is coupled directly to a DMD-based laser refractive surgery system. Turning now to FIG. 8, more particularly, the real-time system 210 includes a computer system 220, a laser 222 for producing a laser beam capable of making refractive corrections, an optical system 224 for shaping and conditioning the laser beam, a DMD 226, and an eye tracking system 228, each substantially similar to the components described above. The system 210 also includes a dual wavelength beamsplitter 242 positionable between the DMD 226 and the eye 240 of the patient. In addition, the system 210 includes an integrated wavefront sensor system 212 coupled to said computer system with a data cable or wireless transmitter, which operates at a wavelength different than the refractive laser. The wavefront sensor system 212 generally includes a Hartmann-Shack sensor (HSS), a CCD camera to record the HSS optical signals, a deformable mirror controlled by the computer 220, and a video frame grabber board coupled to the computer 220 to capture the CCD data. Alternatively, the wavefront sensor system 212 may include its own dedicated computer system. The beamsplitter 242 is adapted to transmit the wavelength of the refractive laser (e.g., UV wavelengths) therethrough, but to reflect light wavelengths used by the wavefront sensor system (e.g., visible wavelengths). The wavefront sensor system 212 directs its light toward the beamsplitter, and the beamsplitter redirects the light to the eye 240 and then back to the wavefront sensor system.

Figure 9:
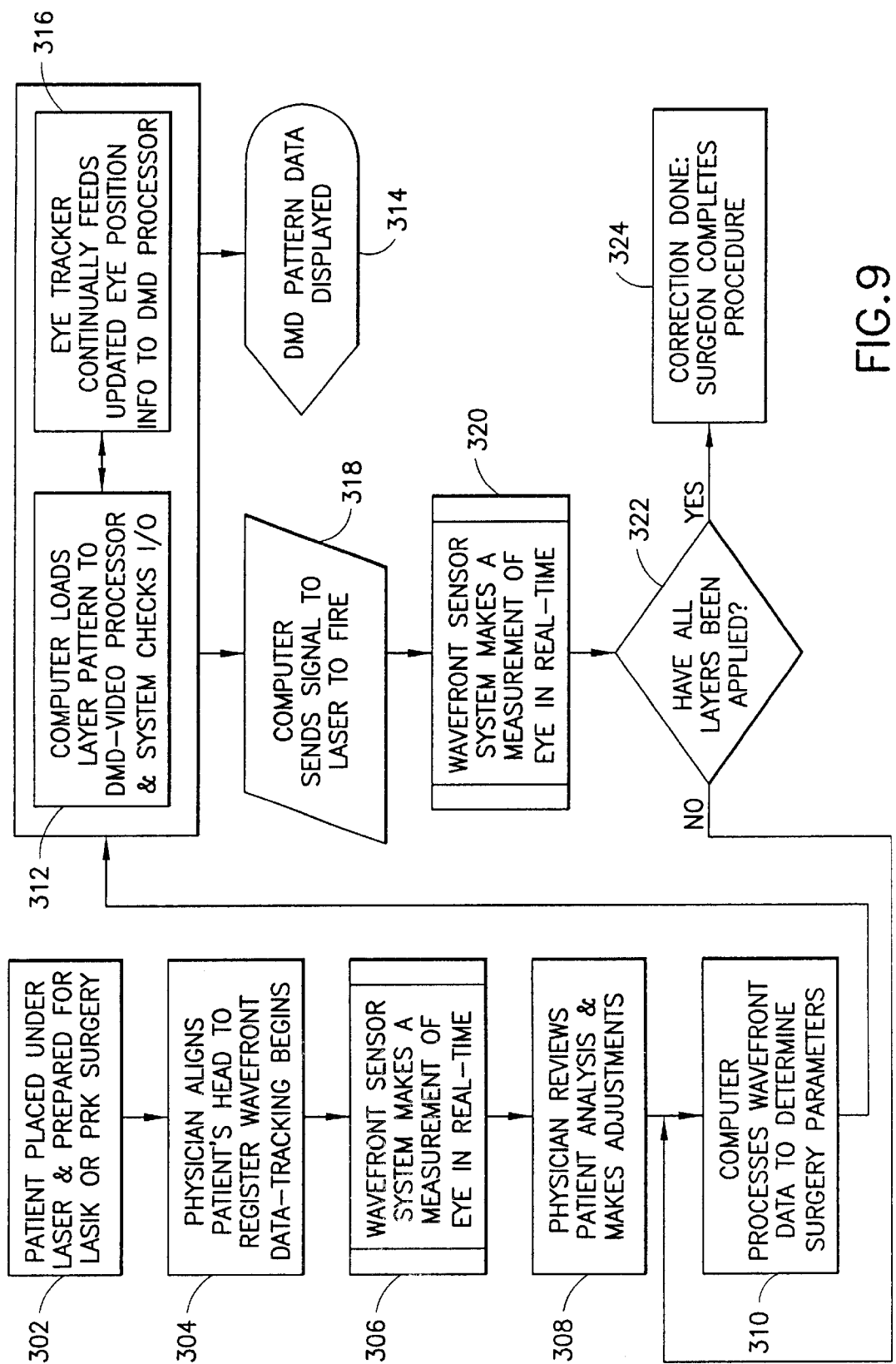
FIG. 9 is a flowchart of a laser ablation or reshaping procedure according to the real-time configuration of the laser ablation or reshaping system of the invention.

Turning now to FIG. 9, in accord with the method of the second embodiment of the invention, the surgeon exposes the corneal stroma tissue via either a LASIK or PRK technique at 302, and the patient is placed under the beamsplitter 242. The surgeon then aligns the patient's head, and thus the eye, at 304, and the wavefront sensor system 212 is then operated at 306 to take an initial measurement of the eye optical system, including registration marker information. Once the registration marker information is gathered, the eye tracking system takes over eye alignment; i.e., the eye tracker 228 constantly provides feedback which may be used to adjust the DMD mirrors to account for eye movement.

The surgeon then reviews and, if necessary, adjusts the analysis at 308. After the analysis has been approved, the wavefront analysis is provided at 310 to the computer system 220. The computer system 220 estimates the number of layers/pulses required to implement the correction (based on the energy density and wavelength used) and creates the image patterns for the layers of ablation or reshaping.

Then, at 312, the computer adjusts the mirrors of the DMD 226 to deliver the appropriate pattern to the cornea for the first layer of the correction, and likewise provides the pattern to a video monitor, at 314. The input parameters are also checked at 312. Meanwhile, the eye tracker 228 is constantly providing feedback at 316 as to the location of the eye. Once all input parameters have been approved, the last measured location of the eye is used to offset the pattern on the DMD mirrors such that the laser beam is appropriately directed.

The computer system 220 then fires at 318 a broadbeam pulse of laser light onto the DMD which then directs the laser energy only to those areas of the cornea identified for reshaping or etching within that layer.

The wavefront sensor then takes another measurement of the eye optical system at 320 and provides that information to the computer system 220, or, alternatively, the computer system may cause several layers of reshaping to occur before another measurement of the eye optical system is taken.

The process repeats at 322 with the computer system adjusting the DMD mirrors into appropriate patterns and subsequent application of laser energy until the wavefront sensor determines that the corneal surface is optimized and no more layers of the cornea need to be corrected. The multiple wavefront analyses of the eye throughout the procedure provide feedback which enables a higher order refractive correction to the cornea and the optical system of the eye.

To complete the procedure at 324, the surgeon applies a contact lens for PRK or repositions the corneal flap for LASIK.

With this system and method, the eye surface may be corrected in a manner superior to prior art systems and methods. The systems have none of the disadvantages associated with prior broadbeam and scanning spot systems. The wavefront sensing system provides an overall refractive analysis of the entire eye optical system, e.g., taking into account the cornea, the lens, the vitreous and the retina. The result of the wavefront sensor analysis yields a waveform model that represents a nearly perfect refraction correction. This provides a superior analysis of the eye relative to the current topography systems which only analyze the cornea and permits correction to the cornea which considers the effect of corneal reshaping on the eye's optical system as a whole. Moreover, the DMD is capable of translating the superior refraction of the wavefront sensor system into highly reliable and quick vision correction.

In each of the above described embodiments a pulsed beam laser (e.g., the excimer laser) having a short pulsed output, typically 10 nanoseconds, has been described. In addition, the mirrors of the DMD have been described as creating patterns in which the mirrors are in either an OFF state or an ON state, and all the mirrors in the ON state are in an ON state at the same time. In accord with another aspect of the invention, the laser surgery system of the invention may be modified as now described. As an alternative to a pulsed beam laser, a relatively low energy continuous wave laser which provides a continuous beam may be used. In addition, the mirrors of the DMD can be controlled to be in either an ON or OFF state at a rate of at least 10 KHz. The energy of the laser and the rate of control of the mirrors is preferably such that the mirrors can change state at least approximately ten times, and preferably at least approximately 50 to 200 times within a preferably 0.01 to 0.0001 second continuous application of the laser beam. As such, when using a continuous wave laser, the mirrors of the DMD may be individually controlled to "dither" the image patterns defined by the wavefront sensor analysis on the corneal stroma. In this manner, the amount of reshaping or ablation of the cornea may be controlled by providing some mirrors in an ON state for a first amount of time where greater amounts of reshaping or ablation are required, and providing other mirrors in an ON state for a lesser amount of time where lesser amounts of reshaping or ablation are required, and providing yet other mirrors in a continuously OFF state where no ablation is required. That is, particular areas of the pattern formed by the mirrors of the DMD may direct the laser for a longer period of time on the exposed corneal surface, while other mirrors direct the laser for a relatively shorter period of time. As a result, corneal reshaping or ablation is provided at different degrees at different locations within the pattern projected on the cornea, providing a similar effect to reshaping or ablating with a series of patterns in a pulsed beam approach.

In a variation on the above described alternative, a continuous laser beam is focused to a width which covers only a portion of the pattern of the mirrors of the DMD. For example, the laser beam may have a width of one percent of the area of the DMD mirror array. The laser beam is scanned across the DMD, e.g., in sequential rows, using known scanning technology such that the laser beam is reflected to any particular portion of the cornea being treated only a fraction of the time, e.g., one percent of the time, the laser beam is directed to a particular mirror element or group of mirror elements of the DMD. In this manner, relatively higher energy continuous wave laser beams may be used without causing unintended damage to the eye.

There have been described and illustrated herein embodiments of a laser eye surgery system using wavefront sensor analysis to control mirror patterns in a digital micromirror device, and methods of using the same. While particular embodiments of the invention have been described, it is not intended that the invention be limited thereto, as it is intended that the invention be as broad in scope as the art will allow and that the specification be read likewise. Thus, while particular excimer, infrared, and continuous wave laser systems have been disclosed, it will be appreciated that other types of lasers suitable for corneal correction, e.g., a YAG-based laser, may be used as well. In addition, for purposes of clarity, "ablating", "reshaping", and "removing", and their conjugates are used interchangeably within the claims. It will therefore be appreciated by those skilled in the art that yet other modifications could be made to the provided invention without deviating from its spirit and scope as claimed.

What is claimed is:

1. A laser surgery system for reshaping the corneal surface of the eye, said system comprising:
   a) a computer system adapted to define a three-dimensional correction for the eye based on wavefront sensor analysis data of the eye;
   b) means for creating a sequence of two-dimensional patterns from said three dimensional correction;
   c) a laser coupled to said computer system and adapted to reshape a portion of a cornea of the eye; and
   d) a digital micromirror device (DMD) having a plurality of mirrors, said mirrors of said DMD being driven into said sequence of two dimensional patterns such that a laser beam produced by said laser is modulated to reshape the cornea of the eye according to said correction.

2. A system according to claim 1, wherein:
   said wavefront analysis data is a three dimensional analysis of the optical system of the eye.

3. A system according to claim 1, further comprising:
   d) a wavefront sensor analysis system which generates said wavefront sensor analysis data, said wavefront sensor analysis system being coupled to said computer system.

4. A system according to claim 3, wherein:
   said laser is adapted to produce a laser light beam at a first wavelength, said wavefront sensor analysis system is adapted to use a light beam at a second wavelength different than said first wavelength, and said laser surgery system further includes a beamsplitter adapted to split said light at said first wavelength from said light said second wavelength.

5. A system according to claim 1, further comprising:
   d) a wavefront sensor analysis system which generates said wavefront sensor analysis data; and
   e) means for providing said wavefront analysis data to said computer system, said means for providing comprising one of a removable storage media, a computer network, a data cable, and a wireless transmitter.

6. A system according to claim 1, wherein:
   each of said patterns of said sequence of two dimensional patterns represents tissue to be reshaped or removed from the cornea at different layers of the cornea.

7. A system according to claim 6, wherein:
each pattern in said sequence of two dimensional patterns is unique.

8. A system according to claim 1, further comprising:
   d) an eye tracking system adapted to track movement of the eye, wherein said computer system defines a sequence of patterns representing locations at which a laser beam produced by said laser is to be directed to reshape or remove tissue from the cornea, and is adapted to drive said mirrors of DMD into said sequence of patterns, and
   wherein said eye tracking system provides feedback to said computer system to offset said patterns on said plurality of mirrors of said DMD according to movement of the eye.

9. A system according to claim 1, wherein:
said laser is one of an excimer laser and a YAG laser.

10. A system according to claim 1, wherein:
said laser is one of a pulsed beam laser and a continuous wave laser.

11. A method for correcting the shape of a cornea of an eye to improve vision, said method comprising:
   a) providing a laser surgery system adapted to perform corrective surgery on the cornea of the eye, said laser surgery system including a laser and a digital micromirror device (DMD) including a plurality of mirrors adapted to modulate a laser beam produced by said laser, said DMD positionable between said laser and the eye;
   b) providing wavefront analysis data representing information about the eye;
   c) utilizing said wavefront analysis data to define a sequence of patterns for said laser beam, each of said patterns representing a particular layer of the cornea to be corrected;
   d) directing said mirrors of said DMD to form a first of said sequence of patterns;
   e) firing said laser at said DMD such that said laser beam is directed by said DMD to contact said cornea in said first of said sequence of patterns; and
   f) repeating said directing said mirrors of said DMD and firing said laser for a next of said sequence of patterns.

12. A method according to claim 11, further comprising:
repeating said directing said mirrors and said firing for all patterns in said sequence of patterns.

13. A method according to claim 11, further comprising:
prior to firing said laser a first time, exposing a corneal stroma of the cornea.

14. A method according to claim 11, wherein:
said exposing includes one of
   i) cutting a flap across the corneal stroma and bending the flap back to expose the corneal stroma, and
   ii) removing an epithelial layer of the cornea.

15. A method according to claim 11, further comprising:
after firing said laser for each of said remaining sequence of patterns, covering said corneal stroma.

16. A method according to claim 11, wherein:
prior to utilizing said wavefront analysis data, adjusting said wavefront analysis data.

17. A method according to claim 11, further comprising:
after said directing and said firing, repeating said providing and utilizing in order to modify said sequence of patterns.

18. A method according to claim 11, wherein:
said wavefront analysis includes registration information facilitating relating said wavefront analysis to a moving eye.

19. A method according t o claim 11, wherein:
said directing said mirrors of said DMD to form a first of said sequence of patterns includes adjusting said mirrors according to movement of the eye.

20. A method according to claim 11, wherein:
said firing includes scanning said laser beam across said DMD.

21. A method for correcting the shape of a cornea of an eye to improve vision, said method comprising:
   a) providing a laser surgery system adapted to perform corrective surgery on the cornea of the eye, said laser surgery system including a laser and a digital micromirror device (DMD) including a plurality of mirrors adapted to modulate a laser beam produced by said laser, said DMD positionable between said laser and the eye;
   b) providing wavefront analysis data representing information about the eye;
   c) utilizing said wavefront analysis data to define a sequence of patterns for said laser beam, each of said patterns representing a particular layer of the cornea to be corrected;
   d) directing said mirrors of said DMD to form a sequence of patterns, said sequence formed by providing a first plurality of said mirrors in an ON state for a first amount of time and by providing a second plurality of mirrors in an ON state for a second amount of time different than said first amount of time, wherein neither said first amount of time nor said second amount of time is a zero amount; and
   e) firing said laser at said DMD such that said laser beam is directed by said DMD to contact said cornea in said sequence of patterns.

22. A method according to claim 21, wherein:
said sequence formed by further providing a third plurality of said mirrors in an ON state for a zero amount of time.

23. A method according to claim 21, wherein:
said laser is a continuous wave laser.

24. A laser surgery system for reshaping the corneal of the eye, said system comprising:
   a) a wavefront sensor analysis system which generates wavefront sensor analysis data;
   b) a computer system coupled to said wavefront sensor analysis system and adapted to define a correction for the eye based on said wavefront sensor analysis data;
   c) a laser coupled to said computer system and adapted to reshape a portion of a cornea of the eye;
   d) a digital micromirror device (DMD) having a plurality of mirrors adapted to modulate a laser beam produced by said laser such that the cornea of the eye is reshaped according to the correction; and
   e) a beamsplitter positioned in a first optical path between said DMD and the eye, and in a second optical path between said wavefront sensor analysis system and the eye,
   wherein said laser is adapted to produce a laser light beam at a first wavelength, said wavefront sensor analysis system is adapted to generate a light beam at a second wavelength different than said first wavelength, and said beamsplitter is adapted to transmit said laser light beam at said first wavelength from said laser to the cornea of the eye and to reflect said light beam at said second wavelength of light from said wavefront sensor analysis system to the eye and further reflect light at said second wavelength from the eye back to said wavefront sensor analysis system.

25. A laser surgery system for reshaping the corneal of the eye, said system comprising:

a) a wavefront sensor analysis system which generates wavefront sensor analysis data incorporating an alignment marker which correlates the data with a physiological location on the eye;

b) a computer system coupled to said wavefront sensor analysis system and adapted to define a correction for the eye based on said wavefront sensor analysis data and to define a sequence of ablation patterns based upon said correction;

c) a laser coupled to said computer system and adapted to reshape a portion of a cornea of the eye; and d) a digital micromirror device (DMD) having a plurality of mirrors adapted to modulate a laser beam produced by said laser in a sequence of patterns, wherein said computer is adapted to adjust said mirrors in said patterns based on said alignment marker.

26. A method for correcting the shape of a cornea of an eye to improve vision, said method comprising:

a) providing a laser surgery system adapted to perform corrective surgery on the cornea of the eye, said laser surgery system including a laser and a digital micromirror device (DMD) including a plurality of mirrors adapted to modulate a laser beam produced by said laser, said DMD positionable between said laser and the eye;

b) providing a wavefront sensor;

c) measuring the eye with the wavefront sensor such that wavefront analysis data is provided;

d) utilizing said wavefront analysis data to define a correction profile;

e) creating a sequence of patterns from said correction profile for said laser beam, each of said patterns representing a particular layer of the cornea to be corrected;

f) directing said mirrors of said DMD to form a one or more of said patterns of said sequence of patterns;

g) for each of said patterns into which said mirrors are directed, firing said laser at said DMD such that said laser beam is directed by said DMD to contact said cornea in said pattern; and h) repeating steps c) through g) such that feedback is provided during the course of correcting the shape of a cornea.

27. A method according to claim 26, wherein:

incorporating an alignment marker in said wavefront sensor data which correlates the wavefront sensor data with a physiological location on the eye.

\* \* \* \* \*

UNITED STATES PATENT AND TRADEMARK OFFICE
Certificate

Patent No. 6,394,999                        Patented: May 28, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Roy E. Williams, Collierville, Tennessee; James F. Freeman, Memphis, Tennessee; Jerre M. Freeman, Memphis, Tennessee; and David E. Thomas, Bartlett, Tennessee.

Signed and Sealed this Tenth Day of December 2002.

<div align="right">

LINDA C. M. DVORAK
*Supervisory Patent Examiner*
Art Unit 3739

</div>